(12) United States Patent
Yu (10) Patent No.: US 10,857,294 B2
(45) Date of Patent: Dec. 8, 2020

(54) TRANSFUSION SPEED REGULATOR, TRANSFUSION MONITORING SYSTEM, AND OPERATION METHOD OF THE SAME

(71) Applicant: BOE TECHNOLOGY GROUP CO., LTD., Beijing (CN)

(72) Inventor: Zhanquan Yu, Beijing (CN)

(73) Assignee: BOE TECHNOLOGY GROUP CO., LTD., Beijing (CN)

(*) Notice: Subject to any disclaimer, the term of this patent is extended or adjusted under 35 U.S.C. 154(b) by 465 days.

(21) Appl. No.: 15/794,376

(22) Filed: Oct. 26, 2017

(65) Prior Publication Data

US 2018/0272062 A1 Sep. 27, 2018

(30) Foreign Application Priority Data

Mar. 27, 2017 (CN) .......................... 2017 1 0189068

(51) Int. Cl.
| | | |
|---|---|---|
| *A61M 5/168* | (2006.01) | |
| *A61M 39/28* | (2006.01) | |
| *A61M 5/172* | (2006.01) | |
| *A61M 5/14* | (2006.01) | |

(52) U.S. Cl.
CPC ...... *A61M 5/16881* (2013.01); *A61M 5/1414* (2013.01); *A61M 5/16845* (2013.01); *A61M 5/172* (2013.01); *A61M 39/28* (2013.01); *A61M 2202/0413* (2013.01); *A61M 2205/18* (2013.01); *A61M 2205/3365* (2013.01); *A61M 2205/3584* (2013.01); *A61M 2205/581* (2013.01); *A61M 2205/587* (2013.01)

(58) Field of Classification Search
CPC .......... A61M 5/16813; A61M 5/16845; A61M 5/16877; A61M 5/16881; A61M 39/28; A61M 39/285; A61M 39/286; A61M 2205/3334

See application file for complete search history.

(56) References Cited

U.S. PATENT DOCUMENTS 3,630,481 A * 12/1971 McGay ............... A61M 39/285
251/6
3,749,285 A * 7/1973 Latham, Jr. ........ A61M 5/16845
222/58
2016/0287785 A1* 10/2016 Isaacson ........... A61M 5/16881

FOREIGN PATENT DOCUMENTS

| CN | 102430170 A | 5/2012 |
| CN | 102451498 A | 5/2012 |
| CN | 103845778 A | 6/2014 |

(Continued)

OTHER PUBLICATIONS

English translation of CN103845778A. Retrieved from Espacenet Apr. 8, 2020. (Year: 2014).*
First Chinese Office Action dated Apr. 1, 2019.

*Primary Examiner* — Kami A Bosworth
(74) *Attorney, Agent, or Firm* — Dilworth & Barrese, LLP.; Michael J. Musella, Esq.

(57) ABSTRACT

A transfusion speed regulator, a transfusion monitoring system and an operation method of the transfusion monitoring system are disclosed. The transfusion speed regulator includes a housing, a lead rail, an actuator and a regulating roller. The housing includes a bottom plate; the lead rail is on the housing and is not parallel to the bottom plate; the regulating roller is configured to be moved along the lead rail to regulate a transfusion speed; and the actuator is configured to drive the regulating roller to move.

10 Claims, 6 Drawing Sheets

(56) References Cited

FOREIGN PATENT DOCUMENTS

| CN | 104258486 A | 1/2015 |
| CN | 204364559 U | 6/2015 |
| CN | 204501934 U | 7/2015 |

* cited by examiner

TRANSFUSION SPEED REGULATOR, TRANSFUSION MONITORING SYSTEM, AND OPERATION METHOD OF THE SAME

CROSS-REFERENCE OF RELATED APPLICATION

The present application claims the benefits of Chinese patent application No. 201710189068.2, which was filed on Mar. 27, 2017 and is fully incorporated herein by reference as part of this application.

TECHNICAL FIELD

Embodiments of the present disclosure relate to a transfusion speed regulator, a transfusion monitoring system and an operation method of the transfusion monitoring system.

BACKGROUND

Transfusion is a commonly used treatment for patients in hospitals. During the transfusion, when encountered with careless nurses who fail to timely stop transfusing upon completion of the transfusion, situations such as blood return and skin edema may be occurred and cause adverse effects to patients' health. Currently, transfusion devices adopted by hospitals usually need to rely on nurses, caregivers or patients to monitor transfusion conditions and regulate transfusion speed. When the transfusion is about to be completed, it requires to manually call the nurses so that the nurses pulls out the transfusion needle from patient's body or block the transfusion tube to stop transfusing. If the caregiver or the nurse is not around the patient or the patient is in unalive status near the end of the transfusion, it may easily result in delay of treatment for the patient or result in serious medical accident, which endanger life safety of the patient.

SUMMARY

At least one embodiment of the present disclosure provides a transfusion speed regulator, a transfusion monitoring system and an operation method of the transfusion monitoring system. The transfusion speed regulator can realize automatic regulation of the transfusion speed and can monitor transfusion conditions in real time.

At least one embodiment of the present disclosure provides a transfusion speed regulator, comprising: a housing, a lead rail, an actuator and a regulating roller. The housing comprises a bottom plate; the lead rail is on the housing and is not parallel to the bottom plate; the regulating roller is configured to be moved along the lead rail to regulate a transfusion speed; and the actuator is configured to drive the regulating roller to move.

At least one embodiment of the present disclosure provides a transfusion monitoring system, comprising a transfusion device. The transfusion device comprises the above-mentioned transfusion speed regulator, a detector and a controller. The detector is configured to detect a weight of a transfusion bottle and output the weight. The controller is configured to control the transfusion speed regulator to regulate a transfusion speed according to the weight.

At least one embodiment of the present disclosure provides an operation method of the above-mentioned transfusion monitoring system, comprising: installing a transfusion bottle; detecting a weight of the transfusion bottle and outputting the weight of the transfusion bottle; and regulating a transfusion speed according to the weight.

BRIEF DESCRIPTION OF THE DRAWINGS

In order to clearly illustrate the technical solution of the embodiments of the disclosure, the drawings of the embodiments will be briefly described in the following; it is obvious that the described drawings are only related to some embodiments of the disclosure and thus are not limitative of the disclosure.

FIG. 1b is a schematic diagram illustrating a section of the transfusion speed regulator along A-A' direction in FIG. 1a;

DETAILED DESCRIPTION

In order to make objects, technical details and advantages of the embodiments of the disclosure apparent, the technical solutions of the embodiments will be described in a clearly and fully understandable way in connection with the drawings related to the embodiments of the disclosure. Apparently, the described embodiments are just a part but not all of the embodiments of the disclosure. Based on the described embodiments herein, those skilled in the art can obtain other embodiment(s), without any inventive work, which should be within the scope of the disclosure.

Unless otherwise defined, all the technical and scientific terms used herein have the same meanings as commonly understood by one of ordinary skill in the art to which the present invention belongs. The terms "first," "second," etc., which are used in the description and the claims of the present application for invention, are not intended to indicate any sequence, amount or importance, but distinguish various components. The terms "comprises," "comprising," "comprises," "comprising," etc., are intended to specify that the elements or the objects stated before these terms encompass the elements or the objects and equivalents thereof listed after these terms, but do not preclude the other elements or objects.

In order to keep the following description of the embodiments of the present disclosure clear and concise, detailed explanations of well-known functions and well-known components may be omitted.

Transfusion therapy is one of commonly used treatments in clinical medicines. However, currently, most hospitals and medical institutions have not realized automatic monitoring management of transfusion and automatic regulation of transfusion speed yet. During the transfusion, it requires patients or medical staffs (such as nurses) to observe a residual amount of medical liquids at any time, or requires the medical staffs to make the rounds of wards for inspection at variable intervals so that the medical staffs can reasonably regulate the transfusion speed according to their own experiences, the residual amount of the medical liquids or state of illness of the patients; near the end of the transfusion, the medical staffs have to timely stop transfusing and replace the medical liquids or pull out the transfusion needle. If the medical staffs fail to timely stop the transfusion or pull out the transfusion needle at the end of the transfusion, air may flow into blood vessels to cause air embolism or blood may be coagulated to block the needle, the consequents ranges from delaying the treatment of the patient and causing the patient's pain, to endangering the patient's life health, resulting in serious medical accident and giving rise to medical disputes.

At least one embodiment of the present disclosure provides a transfusion speed regulator, comprising: a housing, a lead rail, an actuator and a regulating roller. The housing comprises a bottom plate; the lead rail is disposed on the housing and is not parallel to the bottom plate; the regulating roller is configured to be moved along the lead rail to regulate a transfusion speed; the actuator is configured to drive the regulating roller to move.

At least one embodiment of the present disclosure further provides a transfusion monitoring system, comprising a transfusion device. The transfusion device comprises the above-mentioned transfusion speed regulator, a detector and a controller. The detector is configured to detect a weight of a transfusion bottle and output the weight. The controller is configured to control the transfusion speed regulator to regulate a transfusion speed according to the weight.

At least one embodiment of the present disclosure further provides an operation method of the above-mentioned transfusion monitoring system, comprising: installing a transfusion bottle; detecting a weight of the transfusion bottle and outputting the weight of the transfusion bottle; and regulating a transfusion speed according to the weight.

The transfusion speed regulator can realize automatic regulation of transfusion speed. The transfusion monitoring system utilizing the transfusion speed regulator can realize real-time monitoring the transfusion conditions and remotely control the transfusion speed regulator to regulate the transfusion speed, thereby reducing or avoiding the occurrence of blood return or skin edema, increasing the safety of transfusion for the patients, improving the quality of medical services of hospitals, ensuring the physical and psychological health of the patients and decreasing medical accidents.

Hereinafter, embodiments of the present disclosure will be described in more details. However, the present disclosure is not intended to be limited to these specific embodiments.

An embodiment of the present disclosure provides a transfusion speed regulator. The transfusion speed regulator comprises a housing, a lead rail, an actuator and a regulating roller. The housing comprises an bottom plate; the lead rail is disposed on the housing and not be parallel to the bottom plate; the regulating roller is configured to be movable along the lead rail to regulate a transfusion speed; and the actuator is configured to to drive the regulating roller to move.

For example, while the regulating roller moves along the lead rail, a distance between the regulating roller and the bottom plate is gradually varied in such a manner that: a minimum distance between the regulating roller and the bottom plate is not greater than two times of a wall thickness of the transfusion tube, and a maximum distance between the regulating roller and the bottom plate is not smaller than an outer diameter of the transfusion tube when the transfusion tube is not compressed.

For example, the lead rail comprises a first lead rail and a second lead rail which are parallel to each other; the regulating roller comprises a shaft and a cylinder; both ends of the shaft are contacted with the first lead rail and the second lead rail, respectively; and the roller body is sleeved onto the shaft and located between the first lead rail and the second lead rail.

It is noted that, the lead rail being not parallel to the bottom plate means that an extending direction of the lead rail forms an angle not equal to zero with relative to the inner surface of the bottom plate. In other words, an angle between a movement direction of the roller body while moving along the lead rail and the inner surface of the bottom plate is not equal to zero.

For example, an extending direction of the shaft is substantially parallel to the bottom plate.

Hereinafter, several examples of the present embodiment will be described in more details.

Figure 1A:
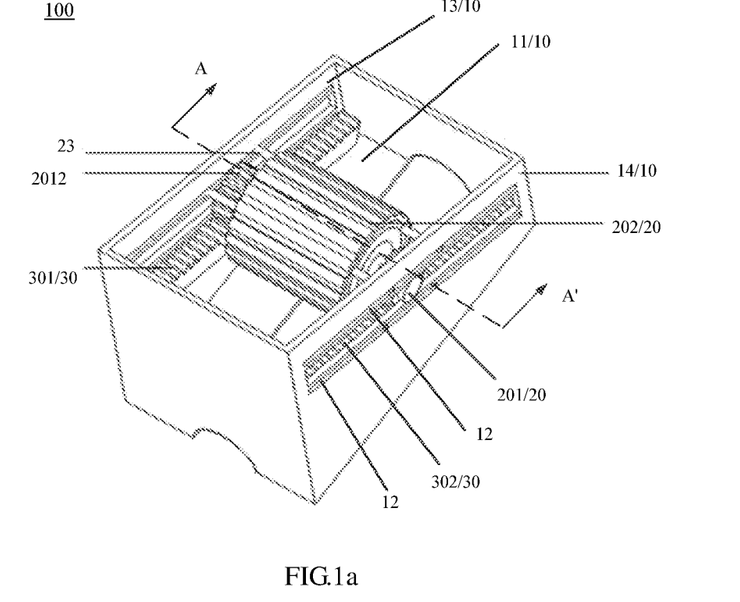
FIG. 1a is a schematic diagram of a transfusion speed regulator provided by an embodiment of the present disclosure.
Figure 1B:
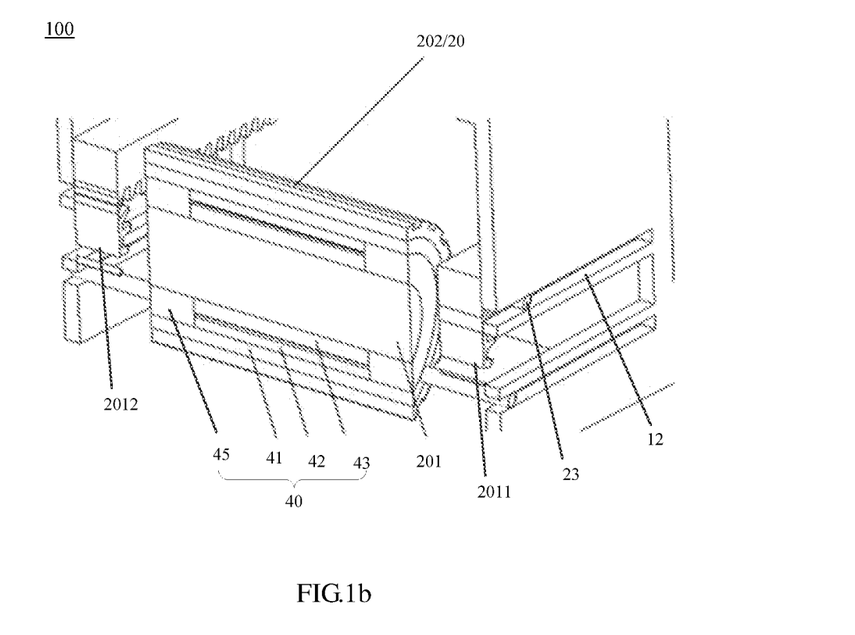

FIG. 1a illustrates a structural schematic diagram of a transfusion speed regulator provided by a first example of the present embodiment; and FIG. 1b is a structural schematic diagram illustrating a section of the transfusion speed regulator along A-A' direction in FIG. 1a.

For example, as illustrated in FIG. 1a and FIG. 1b, in the first example, the transfusion speed regulator 100 comprises a housing 10, a lead rail 30, an actuator 40 and a regulating roller 20. The regulating roller 20 may be, for example, sleeved onto the actuator 40.

For example, the housing 10 comprises an bottom plate 11, and may further comprise a first side wall 13 and a second side wall 14 which are parallel to each other; the regulating roller 20 is moved along the lead rail 30 within a cavity formed by the bottom plate 11, the first side wall 13 and the second side wall 14, so as to regulate the transfusion speed.

For example, the lead rail 30 comprises a first lead rail 301 and a second lead rail 302 which are in parallel to each other. The first lead rail 301 is disposed on the first side wall 13, the second lead rail 302 is disposed on the second lead rail 302, and the first lead rail 301 and the second lead rail 302 may be provided with several racks. It is noted that, the first lead rail 301 and the second lead rail 302 may be fixedly coupled to the first side wall 13 and the second side wall 14, respectively (e.g., bonding with adhesives or welding with ultrasonic wave), or may be formed integrally with the first side wall 13 and the second side wall 14, respectively.

For example, the regulating roller 20 comprises a shaft 201 and a roller body 202. The roller body 202 may be sleeved onto the shaft 201 and be located between the first lead rail 301 and the second lead rail 302. Both ends of the shaft 201 may be provided with a first gear 2011 and a second gear 2022, respectively, and both of the first gear 2011 and the second gear 2022 comprises several tooth spaces. The first gear 2011 and the second gear 2012 are contacted with the first lead rail 301 and the second lead rail 302, respectively; and the several tooth spaces may be, for example, arranged in one-to-one correspondence with the several racks on the first lead rail 301 and the second lead rail 302, respectively. The racks on the first lead rail 301 and the second lead rail 302 are engaged with the tooth spaces on the first gear 2011 and the second gear 2012, respectively, so that the first gear 2011 and the second gear 2012 is capable of rolling on the first lead rail 301 and the second lead rail 302, respectively, in an engaged manner, thereby driving the roller body 202 to be moved along the lead rail 30. The racks and the tooth spaces that are engaged with each other can further increase contacting areas of the first gear 2011 and the second gear 2012 in contact with the first lead rail 301 and the second lead rail 302, respectively, so as to prevent the first gear 2011 and the second gear 2012 from freely sliding on the first lead rail 301 and the second guiding rail 302 due to non man-made factors, thereby controlling the position of the roller body 202 in a better way and ensuring the accuracy of regulating the transfusion speed.

It is noted that, the racks on the first lead rail 301 may be the same as or may be different from the racks on the second lead rail 302, as long as the racks on the first lead rail 301 and the second lead rail 302 are engaged with the tooth spaces on the first gear 2011 and the second gear 2012, respectively, without particularly defined herein. For example, the racks on the first lead rail 301 may be racks with straight tooth, while the racks on the second lead rail 302 may be racks with skewed tooth, accordingly, the first gear 2011 may be a straight cylindrical gear and the second gear 2012 may be a skewed cylindrical gear.

For example, a surface of the roller body 201 is further provided with a plurality of tooth-shaped protrusions so as to increase a friction force generated between the roller body 202 and the transfusion tube, thereby ensuring that the roller body 202 will not freely slide due to non man-made factors and hence ensuring the accuracy of regulating the transfusion speed.

For example, the roller body 202 may be cylinder, or may be cuboid. The cuboid roller body 202 can, for example, increase a contacting area of the roller body 202 in contact with the transfusion tube, increase the friction force generated at the contact position, and prevent the roller body 202 from freely sliding, so as to ensure the stability and accuracy of regulating the transfusion speed.

For example, in a direction extending along the lead rail 30, the transfusion tube penetrates through the housing 10 and be located between the bottom plate 11 of the housing 10 and the roller body 202 of the regulating roller 20. The lead rail 30 is not parallel to the bottom plate 11, so that during the regulating roller 20 moving along the lead rail, a distance between the roller body 202 and the bottom plate 11 is gradually varied in such a manner that: a minimum distance between the roller body 202 and the bottom plate 11 is not greater than two times of a wall thickness of transfusion tube, and a maximum distance between the roller body 202 and the bottom plate 11 is not smaller than an outer diameter of the transfusion tube when the transfusion is not compressed. In this way, in the direction extending along the lead rail 30, the roller body 202 presses the transfusion tube or loosen the transfusion tube, so as to regulate the transfusion speed. For example, when the roller body 202 is located to have the maximum distance from the bottom plate 11, the transfusion tube is not compressed, and the transfusion speed at this moment will be highest such that medical liquids can completely flow through the transfusion tube; when the roller body 202 is located to have the minimum distance from the bottom plate 11, the transfusion tube is completely compressed, and the transfusion speed at this moment will be the smallest such that the medical liquids cannot flow through the tube at a position where the roller body 202 is contacted with the transfusion tube, and the transfusion will be stopped.

For example, at the position where the bottom plate 11 has the minimum distance from the roller body 202, the bottom plate 11 is provided with a recess having a shape matched with the roller body 202, so as to allow the transfusion tube to be bent upon compressed to ensure pinch-off effect of the transfusion tube.

It should be noted that, in the present embodiment, the "maximum distance" and the "minimum distance" both refer to a distance between a plane of the bottom plate 11 except for the recess and a surface of the roller body 202 facing the bottom plate 11; that is, a distance between an inner surface of the bottom plate 11 to be in contact with the transfusion tube and a surface of the roller body 202 facing the bottom plate 11. The wording "not greater than" refers to that the minimum distance between the roller body 202 and the bottom plate 11 is smaller than or equal to two times of the wall thickness of the transfusion tube, as long as it can pinch off the transfusion tube. For example, when the minimum distance between the roller body 202 and the bottom plate 11 is smaller than two times of the wall thickness of the transfusion tube, the transfusion tube may be compressed to deform, so as to further ensure the pinch-off effect of the transfusion tube. The wording "not smaller than" refers to that the maximum distance between the roller body 202 and the bottom plate 11 is greater than or equal to the outer diameter of the transfusion tube when not compressed, as long as it allows the medical liquids to completely flow through the transfusion tube. It is noted that, the wording "equal to" may refer to "substantially equal to".

For example, the lead rail 30 may be perpendicular to the bottom plate 11 so as to reduce a volume of the transfusion speed regulator 100 and save the cost.

For example, the actuator 40 is a DC motor or an AC motor, and the actuator 40 comprises a stator 42 and a rotator 43 which are disposed between the shaft 201 and roller body 202. The shaft 201 is fixedly coupled to the rotator 43, and the roller body 202 is sleeved onto the stator 42. The rotator 43 drives the shaft 201 to rotate, and hence drive the first gear 2011 and the second gear 2012 to roll on the first lead rail 301 and the second lead rail 302, respectively, and hence drive the roller body 202 to be moved along the lead rail 30 so as to regulate the transfusion speed.

It should be noted that, when moving along the lead rail 30, the roller body 202 may not be rotated, or may be rotated around an axis of the shaft 201. For example, the roller body 202 may be fixedly coupled with relative to the stator 42 of the actuator 40 so as not to rotate when moving along the lead rail 30; or may be slidably coupled with relative to the stator 42 of the actuator 40 so as to be rotated around the shaft 201.

For example, the actuator 40 further comprises a bearing 45 and a housing 41. The bearing 45 is set on the rotator 43 to guide the rotator 43 to stably rotate and prevent the rotator 43 from shifting during the rotation. The housing 41 is sleeved onto the stator 42, while the roller body 202 is sleeved onto the housing 41; the housing 41 is connected to grounding wires so as to avoid occurrence of electric leakage and also prevent from electric shock when manually regulating the roller body 202.

For example, the transfusion speed regulator 100 further comprises a lead rod 23 and a chute 12. The chute 12 may be disposed on the first side wall 13 and the second side wall 14, and may be extending along a direction parallel to the extending direction of the lead rail 30. The lead rod 23 may be fixedly coupled to the stator 42 and extends into the chute 12. When the rotator 43 is rotated, the lead rod 23 can ensure the first gear 2011 and the second gear 2012 on both ends of the shaft 201 rolling on the first lead rail 301 and the second lead rail 302, respectively, so as to prevent the first gear 2011 from separating from the first lead rail 301 and prevent the second gear 2012 from separating from the second lead rail 302. In addition, the stator 42 is coupled to the lead rod 23, and the lead rod 23 extends into the chute 12, so as to further prevent the stator 42 from rotating and ensure a power output of the actuator 40.

For example, a plurality of the lead rods 23 and a plurality of the chutes 12 may be arranged. As illustrated in FIG. 1a and FIG. 1b, two lead rods 23 are disposed on each end of the roller body 202, and two chutes 12 are respectively disposed on the first side wall 13 and the second side wall 14. The plurality of lead rods 23 and the plurality of chutes 12 can further ensure the first gear 2011 and the second gear 2012 respectively rolling on the first lead rail 301 and the second lead rail 302 in a stable manner, so as to prevent the roller body 202 from tilt or wrapping, and to increase the accuracy of regulating the transfusion speed.

Figure 2:
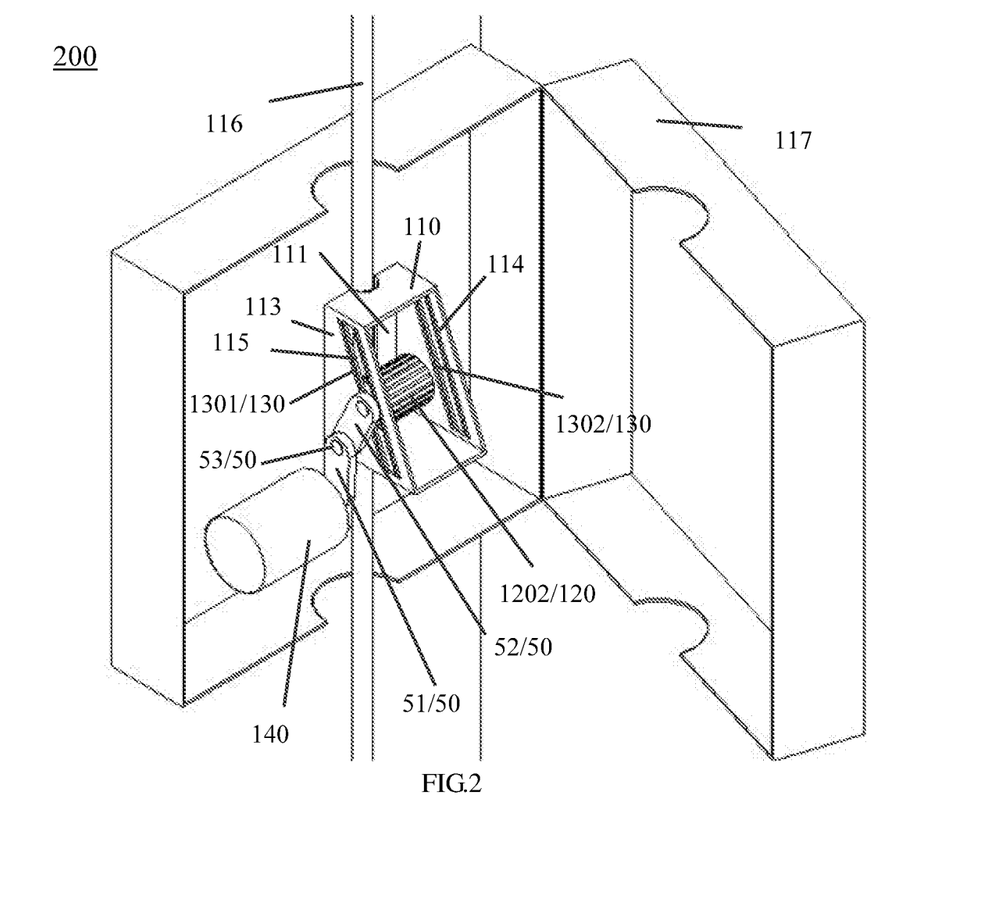
FIG. 2 is a schematic diagram of another transfusion speed regulator provided by an embodiment of the present disclosure.

FIG. 2 illustrates a structural schematic diagram of a transfusion speed regulator provided by a second example of the present embodiment.

As illustrated in FIG. 2, in the second example, the transfusion speed regulator 200 comprises: a housing 110, a lead rail 130, an actuator 140, a regulating roller 120 and a linkage component 50. The actuator 140 and the regulating roller 120 may be coupled to each other through, for example, the linkage component 50.

For example, the housing 110 comprises a bottom plate 111, a first side wall 113 and a second side wall 114. The regulating roller 120 may be moved along the lead rail 130 within a cavity formed by the bottom plate 111 with the first side wall 113 and the second side wall 114, so as to regulate the transfusion speed.

For example, the lead rail 130 is disposed on the housing 110 and is not parallel to the bottom plate 111. The lead rail 130 may be, for example, perpendicular to the bottom plate 111 so as to decrease the volume of the transfusion speed regulator 200 and save the cost. The lead rail 130 comprises a first lead rail 1301 and a second lead rail 1302 which are disposed in parallel to each other. The first lead rail 1301 is, for example, disposed on the first side wall 113, and the second lead rail 1302 is, for example, disposed on the second side wall 114. It is noted that, the first lead rail 1301 and the second lead rail 1302 may be fixedly coupled to the first side wall 113 and the second side wall 114, respectively, or may be formed integrally with the first side wall 113 and the second side wall 114, respectively.

For example, the regulating roller 120 is moved along the lead rail 130 so as to regulate the transfusion speed. The regulating roller 120 comprises a shaft (not illustrated) and a roller body 1202 sleeved onto the shaft. The shaft and the roller body 1202 may be integrally disposed, and the roller body 1202 is located between the first lead rail 1301 and the second lead rail 1302. Both ends of the shaft is, for example, provided with a first gear (not illustrated) and a second gear (not illustrated), respectively; and the first gear and the second gear may be respectively contacted with the first lead rail 1301 and the second lead rail 1302 so as to be moved along the first lead rail 1301 and the second lead rail 1302, respectively. However, the embodiments of the present disclosure are not limited thereto. The two ends of the shaft may not be provided with the gears, and in such case both ends of the shaft may slide or roll on the lead rail 130. Moreover, in the second example, the shaft and the roller body 1202 may be fixedly connected, or the shaft and the roller body 1202 may also be formed integrally.

For example, as illustrated in FIG. 2, in a direction extending along the lead rail 30, the transfusion tube 116 penetrates through the housing and is set between the bottom plate 111 of the housing 110 and the roller body 1202, so that the roller body 1202 can press the transfusion tube 116 or loosen the transfusion tube 116, thereby regulating the transfusion speed.

It is noted that, the roller body 1202 may make a translation movement along the direction of the lead rail 130, and may also make a rolling movement along the direction of the lead rail 130. Shapes of the roller body 1202 and the bottom plate 111, as well as relative positions thereof may be the same as that of the first example, which will not be elaborated here.

For example, the actuator 140 is a DC motor or an AC motor, and the actuator 140 has a power output terminal. At least one end of the shaft of the regulating roller 120 may serve as a power input terminal which is coupled to the power output terminal of the actuator 140 through the linkage component 50.

For example, a sliding rail 115 is disposed on the first side wall 113 and the second side wall 114 corresponding to the first lead rail 1301 and the second lead rail 1302, respectively. The sliding rail 115 penetrates through the first side wall 113 and the second side wall 114, respectively; the power input terminal of the shaft of the regulating roller 120 may extend into the sliding rail 115 and be coupled to the power output terminal of the actuator 140 through the linkage component 50, so that the actuator 140 may transmit a driving force to the regulating roller 120 through the linkage component 50 to drive the regulating roller 120 to move along the lead rail 130 to regulate the transfusion speed.

For example, the linkage component 50 comprises a first linkage 51 and a second linkage 52. A first end of the first linkage 51 and a first end of the second linkage 52 may be pivotally coupled to each other through a connecting piece 53. A second end of the first linkage 51 may be coupled to the power output terminal of the actuator 40, and a second end of the second linkage 52 may be coupled to the power input terminal of the shaft.

For example, a pivot connection comprises a flexible connection, a slidable connection or a rotatable connection, as long as it allows the first linkage 51 and the second linkage 52 to be moved with relative to each other for power transmission. For example, the connecting piece 53 may be a lower pair, and then the linkage component 50 may be a dual-linkage mechanism in which the first linkage 51 and the second linkage 52 are pivotally connected through the lower pair. For example, the lower pair comprises a revolute pair, a sliding pair or a spherical pair and the like. If the lower pair is a revolute pair, then the first linkage 51 and the second linkage 52 are rotatably connected to each other.

For example, both ends of the shaft are a power input terminal. The two power input terminals may be connected to the power output terminals of different actuator 140, respectively, and may also be connected to a power output terminal of a same actuator 140. The arrangement of two power input terminals can further ensure driving the regulating roller 120 to stably move along the lead rail 130, accurately controlling the position of the roller body 1202 and further preventing the roller body 1202 from tilting, wrapping and the like, so as to increase the accuracy of regulating the transfusion speed.

It is noted that, shapes of the first lead rail 1301, the second lead rail 1302, the first gear and the second gear may be the same as those in the first example, and may also be different from the first example, without particularly limited herein. For example, the first lead rail 1301 and the second lead rail 1302 may be further provided with several racks, and the first gear and the second gear may be further provided with several tooth spaces which are arranged in one-to-one correspondence with the several racks so that the first gear and the second gear can respectively roll on the first lead rail 1301 and the second lead rail 1302 in an engaged manner, which effectively prevents the first gear and the second gear from freely sliding on the first lead rail 1301 and the second lead rail 1302 due to non man-made factors, thereby controlling the position of the roller body 1202 in a better way and ensuring the stability and accuracy of regulating the transfusion speed. For another example, in a direction perpendicular to the extending direction of the lead rail 130, each of the first lead rail 1301 and the second lead rail 1302 provides a rail arranged at both sides of the sliding rail 115, and the rail on both sides of the sliding rail 115 is provided with several racks so as to further increase the contact areas of the first gear and the second gear contacting with the first lead rail 1301 and the second lead rail 1302, respectively, more effectively prevent the first gear and the second gear from freely sliding, and further increase the stability and accuracy of regulating the transfusion speed.

For example, as illustrated in FIG. 2, the transfusion speed regulator 200 further comprises a protection housing 117. Interior components (e.g., housing 110, lead rail 130, actuator 140, regulating roller 120 and linkage component 50, etc.) of the transfusion speed regulator 200 may be installed within the protection housing 117, so that the protection housing 117 can protect these interior components.

Another embodiment of the present disclosure provides a transfusion monitoring system.

Figure 3:
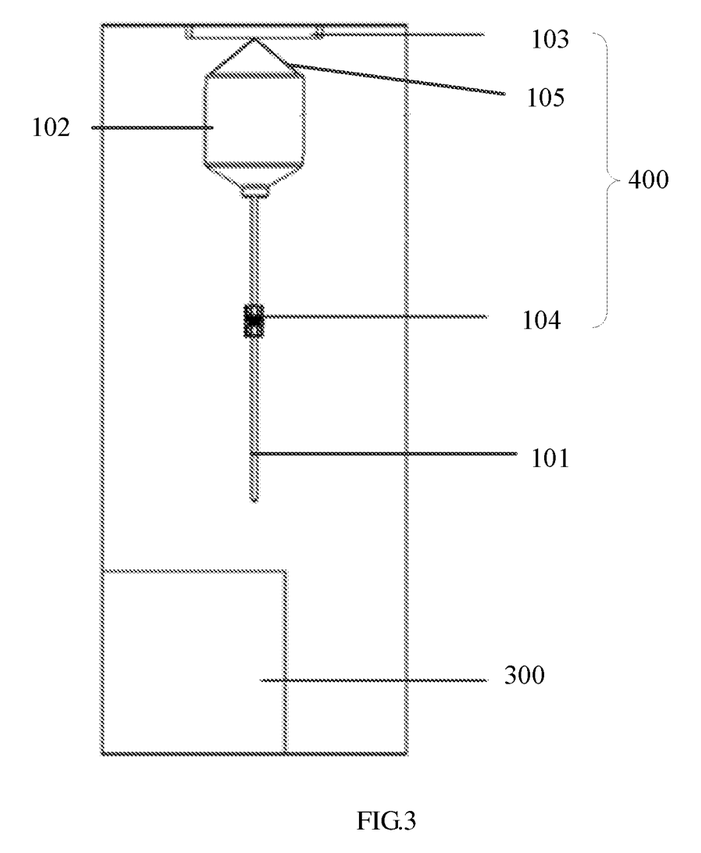
FIG. 3 is a schematic diagram of yet another transfusion monitoring system provided by an embodiment of the present disclosure.
Figure 4:
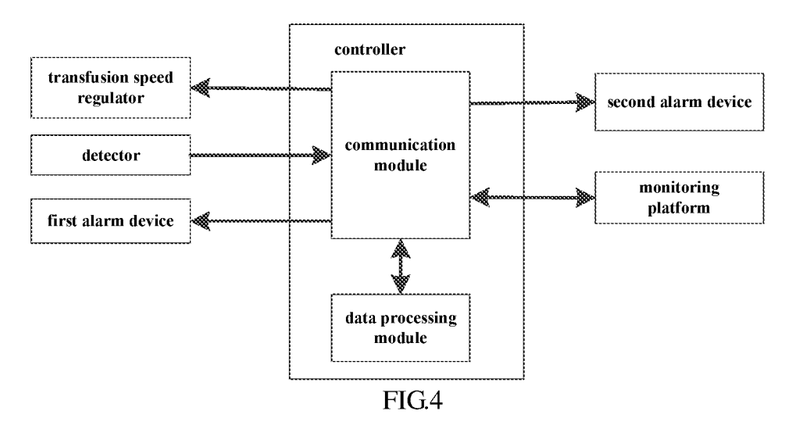
FIG. 4 is a block diagram of a transfusion monitoring system provided by an embodiment of the present disclosure.

FIG. 3 illustrates a structural schematic diagram of a transfusion monitoring system provided by the present embodiment; and FIG. 4 is an illustrative block diagram of a transfusion monitoring system provided by the present embodiment.

For example, as illustrated in FIG. 3, in an example, the transfusion monitoring system provided by the present embodiment comprises a transfusion device 400 which comprises the transfusion speed regulator 104 provided by any of the foregoing embodiments, a detector 103 and a controller (not illustrated). The transfusion device 400 may further comprise a support 105 on which a transfusion bottle 102 may be hanged; the detector 103 may be configured to detect a weight of the transfusion bottle 102 and output the weight; the controller is configured to control the transfusion speed regulator 104 to regulate a transfusion speed according to the weight.

For example, a transfusion tube 101 is installed in the transfusion device 400. For example, the transfusion tube 101 penetrates through the housing 10 of the transfusion speed regulator 104, and the regulating roller 20 of the transfusion speed regulator 104 may press the transfusion tube 101 or loosen the transfusion tube 101 so as to regulate the transfusion speed.

For example, the detector 103 comprises a weighing sensor which may be an electronic weighing sensor or the like. The weighing sensor is capable of detecting the weight of the transfusion bottle 102 in real time and output the weight of the transfusion bottle 102. For example, the detector 103 further comprises a velometer which is configured to detect a dropping speed of medical liquids (e.g., the dropping speed of the medical liquids may be calculated according to a time difference between two drops of medical liquids) and output the dropping speed of the medical liquids, so as to more visually detect the transfusion speed.

For example, the weight of the transfusion bottle 102 may reflect a residual amount of medical liquids in the transfusion bottle 102, and the controller may control the transfusion speed regulator 104 to regulate the transfusion speed according to the weight of the transfusion bottle 102. For example, if the weight of the transfusion bottle 102 is smaller than a first preset weight, the controller may send a first control signal corresponding to the first preset weight to automatically control the transfusion speed regulator 104 to lower the transfusion speed. If the weight of the transfusion bottle 102 is smaller than a second preset weight, the controller may send a second control signal corresponding to the second preset weight to automatically control the transfusion speed regulator 104 to stop the transfusion. For another example, the controller may further control the transfusion speed regulator 104 to regulate the transfusion speed according to the dropping speed of the medical liquids. For example, for the adults, some clinically conventional medicines (e.g., antibiotics, hemostatics and the like) may have a dropping speed ranged from 40 drops per min to 60 drops per min. If the dropping speed is relatively faster (e.g., the dropping speed is approximately 80 drops per min), the regulating roller 20 presses the transfusion tube 101, and a cross-sectional area of the transfusion tube 101 that allows the medical liquids to flow through is decreased so as to lower the transfusion speed. For example, if the dripping speed is relatively slower (e.g., the dropping speed is 20 drops per min), the regulating roller 20 loosens the transfusion tube 101 of and the cross-sectional area of the transfusion tube 101 that allows the medical liquids to flow through is increased so as to raise the transfusion speed.

For example, the first preset weight is greater than the second preset weight. The first preset weight may be one quarter of a total weight of the transfusion bottle 102 full of medical liquids, and the second preset weight may be one fifth of a total weight of the transfusion bottle 102 full of medical liquids. It is noted that, the medical staffs may specifically configure the first preset weight and the second preset weight according to specific conditions of the patient, types of the medical liquids, the temperature of the medical liquids, his own experiences and the like. Moreover, several preset weights may be arranged depending on actual conditions so as to satisfy requirements from various patients, various medical liquids and the like, without limited in the present disclosure.

For example, the controller may be a single chip, a programmable logic controller (PLC) or a central processing unit (CPU) and the like.

For example, the controller comprises a communication module and a data processing module. For example, as illustrated in FIG. 4, the communication module may transmit transfusion information among interior components of the transfusion device 400. The communication module may, for example, receive the weight output from the detector 103; the data processing module processes the weight and gives out a corresponding control signal according to the weight; the control signal is transmitted to the transfusion speed regulator 104 through the communication module so as to regulate the transfusion speed.

For example, the communication module may adopt a wired transmission manner or a wireless transmission manner. The wired transmission manner may, for example, adopt communication ways such as twisted pair communication, coaxial cable communication or optical fiber communication. The wireless transmission manner may, for example, adopt Bluetooth communication, Zigbee communication or WiFi communication. The data processing module may be, for example a digital signal processor.

For example, the transfusion monitoring system may further comprise a monitoring platform 300. The monitoring platform 300 is configured to be able to read the weight output from the detector 103 and send the control signal for regulating the transfusion speed to the controller.

For example, as illustrated in FIG. 4, the communication module may also conduct a transmission of transfusion information between the monitoring platform 300 and the transfusion device 400. The communication module may, for example, receive the weight of the transfusion bottle 102 output from the detector 103 and transmit this weight to the monitoring platform 300; and may further receive a control signal output from the monitoring platform 300 and transmit this control signal to the transfusion speed regulator 104. For example, if the weight of the transfusion bottle 102 is smaller than a first preset weight, the monitoring platform 300 may remotely send a first control signal corresponding to the first preset weight; the communication module receives the first control signal and transmits the first control signal to the transfusion speed regulator 104 so as to control the transfusion speed regulator 104 to lower the transfusion speed.

For example, the transfusion device 400 may be installed in the ward, e.g., on a transfusion bed. The monitoring platform 300 may be disposed in a nursing station so that the medical staffs can monitor the transfusion conditions of the patient at any time. The monitoring platform 300 may also be disposed in a terminal device such as mobile phone or tablet computer so that the medical staffs can monitor the transfusion conditions of the patient at any time and any place. In this way, the medical staffs may monitor the transfusion conditions of the patient in real time even during round of ward, so as to increase the working efficiency of the medical staffs. It is noted that, a single monitoring platform 300 may monitor a plurality of transfusion devices 400 so as to monitor the transfusion conditions of a plurality of patients in real time, which further increases the working efficiency of the medical staffs.

For example, the transfusion monitoring system may further comprise an alarm device which may be disposed on at least one of the transfusion device 400 and the monitoring platform 300. The communication module may further, for example, send the weight to the alarm device, which receives the weight and makes determination so as to output an alarming signal if the weight is smaller than at least one of the first preset weight and the second weight.

It is noted that, the alarming signal may be automatically stopped (e.g., it may be preconfigured such that the alarming signal is stopped upon 2 minutes expiring), or may be manually turned off by the patient or the medical staffs.

For example, the alarm device comprises a first alarm device and a second alarm device. The first alarm device may be disposed at the transfusion device 400 so as to remind the patient or the relatives of the patient of regulating the transfusion speed or calling the medical staffs to proceed with subsequent nursing works. The second alarm device may be disposed at the monitoring platform 300 so as to remind the medical staffs of proceeding with subsequent nursing works. It is noted that, the subsequent nursing works may comprise, for example, regulating the transfusion speed, replacing the medical liquids, inspecting the patients' body conditions, and the like.

For example, if the weight is smaller than the first preset weight, both the first alarm device and the second alarm device may output a first alarming signal; if the weight is smaller than the second preset weight, both the first alarm device and the second alarm device may output a second alarming signal. The first alarming signal and the second alarming signal may be a same alarming signal, and may also be different alarming signals. For example, the alarm device comprises at least one of a buzzer and a light-emitting device. For the first alarming signal, the buzzer may generate discontinuous buzzing, and the light-emitting device may generate twinkling yellow light; while for the second alarming signal, the buzzer may generate continuous buzzing and the light-emitting device may generate twinkling red light, so that the medical staffs or the patient may directly determine the transfusion conditions according to different alarming sounds and/or light signals, and then proceed with subsequent operations (e.g., the medical staffs may regulate the transfusion speed or replace the medical liquids, or the patient may regulate the transfusion speed by himself or call the medical staffs, and the like).

For example, the transfusion monitoring system may further comprise a display which is configured to display transfusion monitoring information. The transfusion monitoring information comprises the weight of the transfusion bottle 102, the dropping speed of the medical liquids and the like, and may further comprise the types of the medical liquids, the temperature of the medical liquids, the time duration of transfusion or the alarming signal and the like, so that the medical staffs can clearly understand the transfusion conditions of the patient based on the display, which facilitates subsequent nursing works; the patient or the relatives of the patient may also monitor the transfusion conditions in real time through the display.

For example, the transfusion monitoring system may further comprise a power supply unit which may supply various components in the transfusion monitoring system with stable electric power. The power supply unit may be an externally connected DC or AC power supply, or may be a battery such as a primary battery or a secondary battery.

The transfusion monitoring system in the present embodiment can monitor the transfusion conditions in real time through the detector 103, and automatically regulate the transfusion speed through the transfusion speed regulator 104 or remotely control the transfusion speed regulator 104, through the monitoring platform, to regulate the transfusion speed, thereby reducing or avoiding the occurrence of blood return or skin edema, increasing the safety of transfusion for the patients, increasing the quality of medical services of hospitals, ensuring the physical and psychological health of the patients and decreasing medical accidents.

Figure 5:
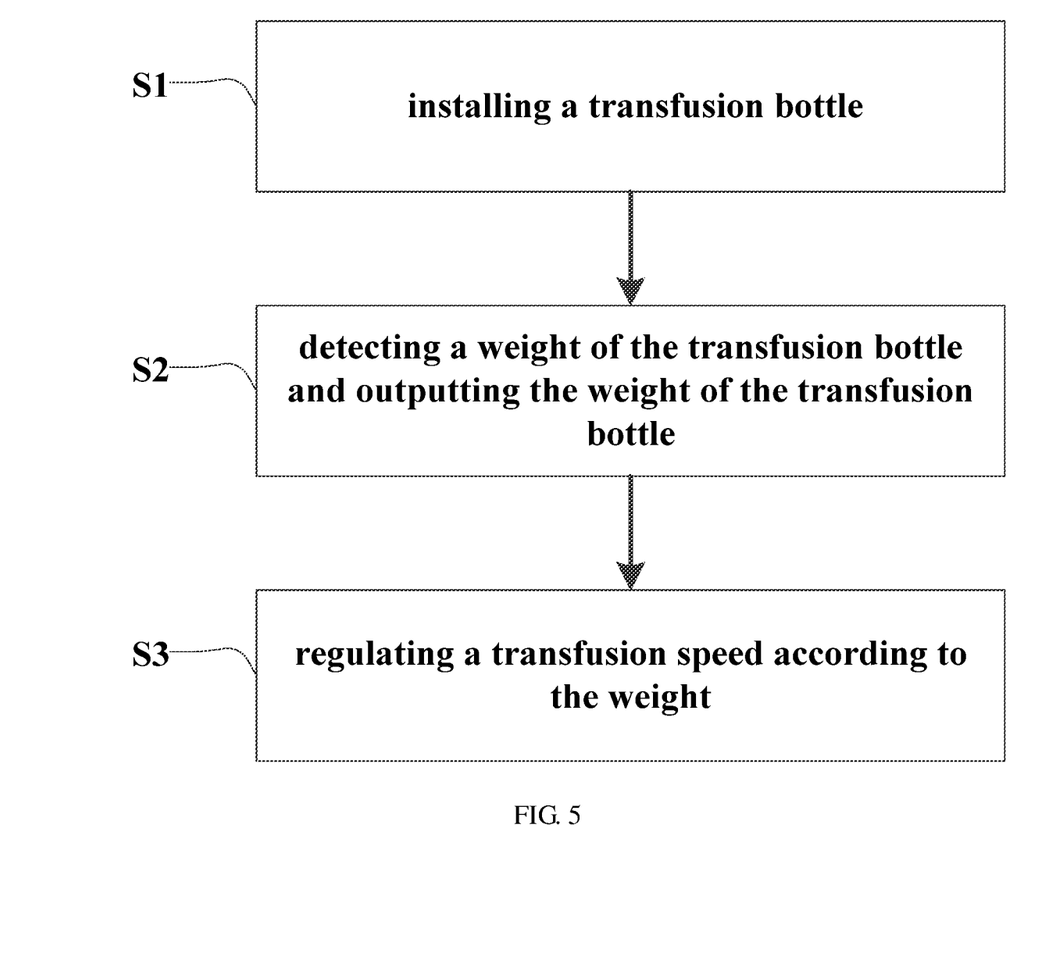
FIG. 5 is a flow chart of an operation method of a transfusion monitoring system provided by an embodiment of the present disclosure.
Figure 6A:
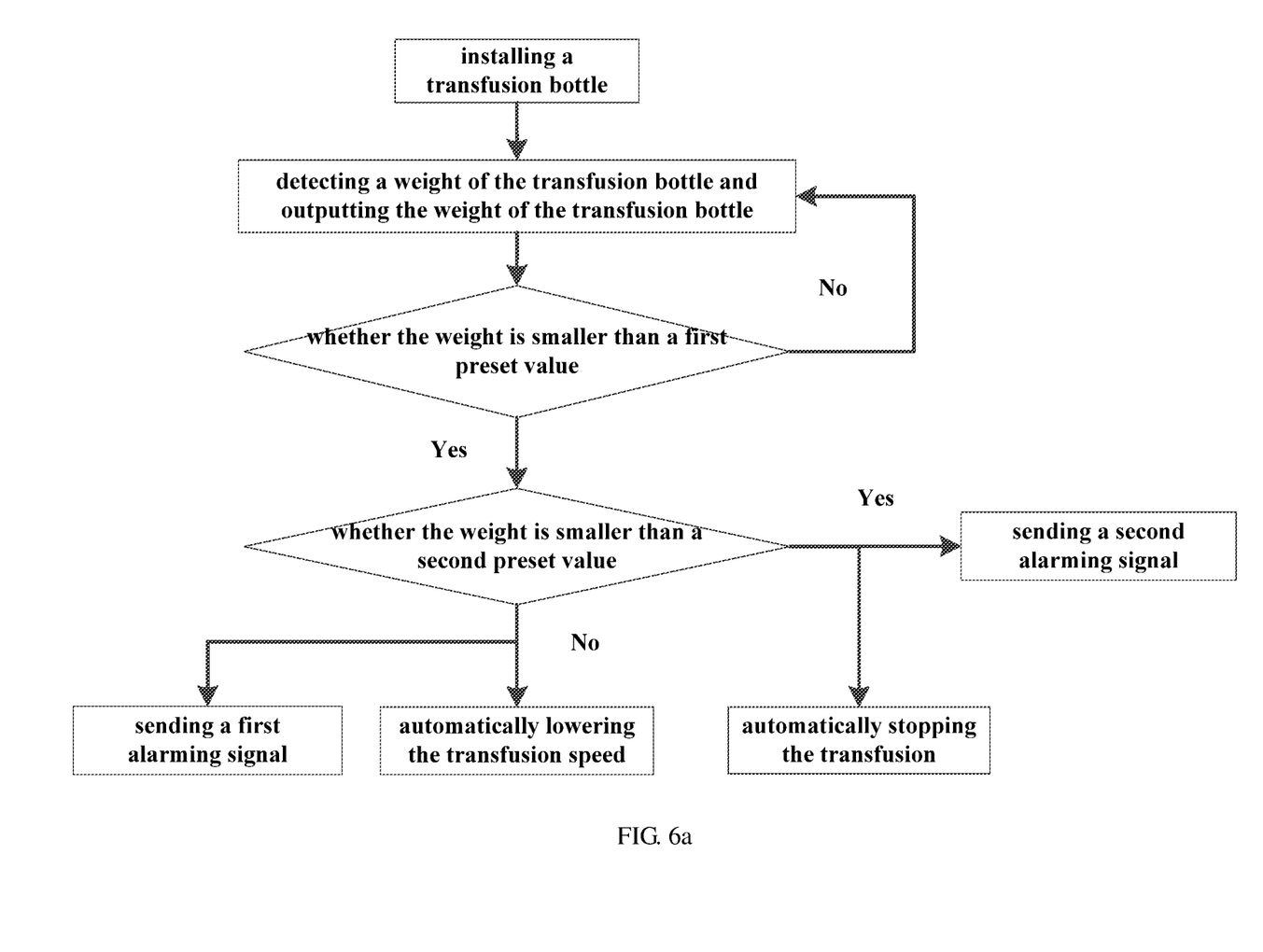
FIG. 6a is a logical flow chart of an operation method of a transfusion monitoring system provided by an embodiment of the present disclosure.
Figure 6B:
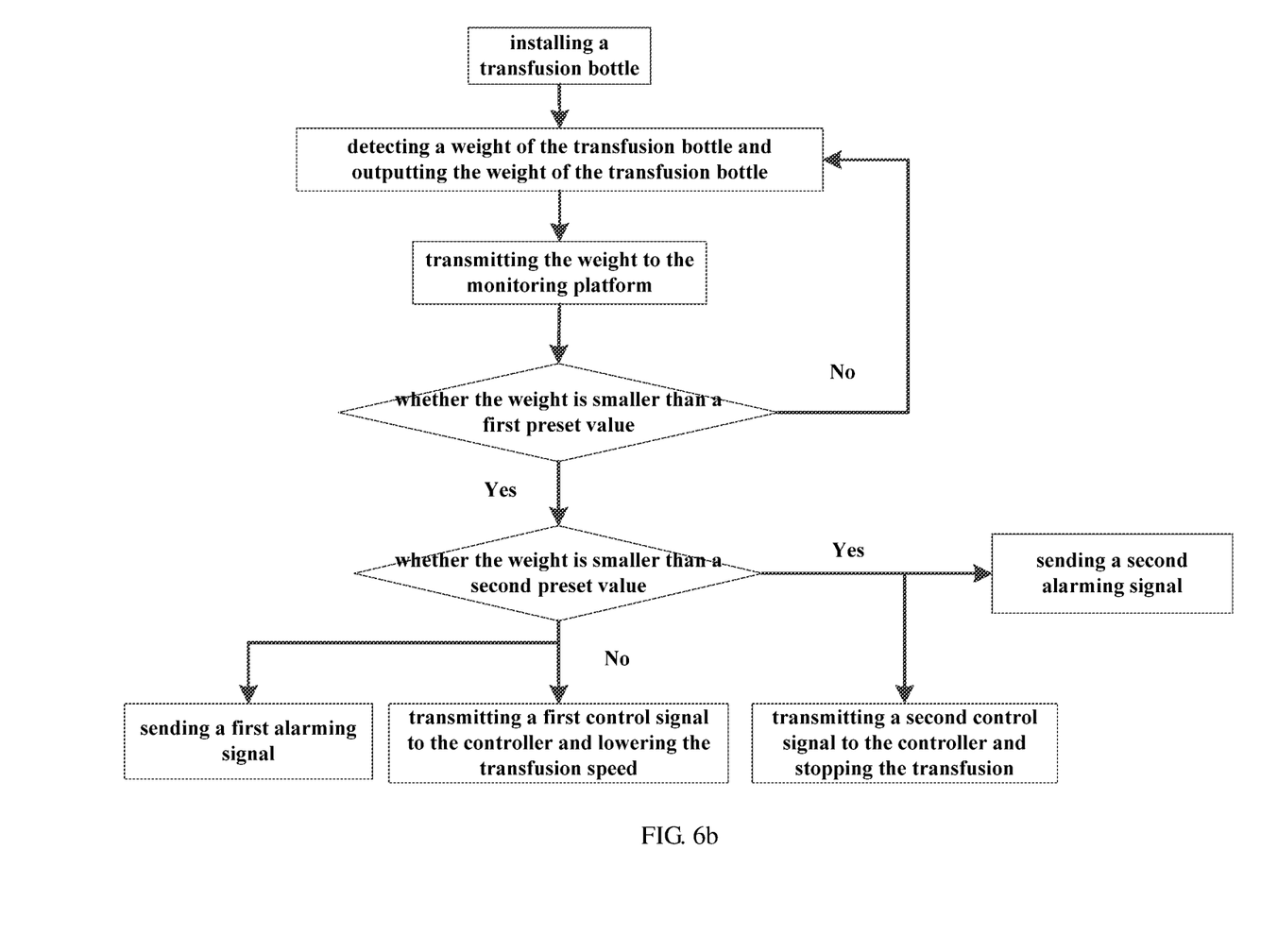
FIG. 6b is a logical flow chart of another operation method of a transfusion monitoring system provided by an embodiment of the present disclosure.

FIG. 5 is an illustrative flow chart of an operation method of a transfusion monitoring system provided by an embodiment of the present disclosure; FIG. 6a is a logical flow chart of an operation method of a transfusion monitoring system provided by another embodiment of the present disclosure; and FIG. 6b is a logical flow chart of an operation method of a transfusion monitoring system provided by yet another embodiment of the present disclosure.

An embodiment of the present disclosure provides an operation method of the transfusion monitoring system of any of the foregoing embodiments or examples. As illustrated in FIG. 5, the operation method comprises:

Step S1, installing a transfusion bottle;

Step S2: detecting a weight of the transfusion bottle and outputting the weight of the transfusion bottle;

Step S3: regulating a transfusion speed according to the weight.

In the operation method provided by the present embodiment, the detector 103 may be adopted to detect the weight of the transfusion bottle 102 in real time and output the weight of the transfusion bottle. For example, the transfusion bottle is filled with liquid medicine, and the weight being detected is equal to a sum of the weight of the bottle body and the weight of the liquid medicine. Then the controller may be adopted to receive the weight and automatically control the transfusion speed regulator 104 to regulate the transfusion speed according to a magnitude of the weight; alternatively, the controller may be adopted to transmit the weight to the monitoring platform 300 which receives the weight and transmits a corresponding control signal to the controller so as to remotely control the transfusion speed regulator 104 to regulate the transfusion speed. In this way, the transfusion monitoring system can monitor the transfusion conditions in real time, and automatically regulate the transfusion speed, thereby reducing or avoiding the occurrence of blood return or skin edema, increasing the safety of transfusion for the patients, improving the quality of medical services of hospitals, ensuring the physical and psychological health of the patients and decreasing medical accidents.

For example, prior to the step S3, the operation method of the present embodiment may further comprise: setting a preset weight. The preset weight may, for example, comprise a first preset weight and a second preset weight, and the first preset weight is greater than the second preset weight. If the weight is smaller than the first preset weight, the transfusion speed is lowered; if the weight is smaller than the second preset weight, the transfusion is stopped. It is noted that, the preset weights may comprises more than two preset weights so as to satisfy requirements from various patients, various medical liquids and the like.

For example, in the operation method of the present embodiment, the step S3 may further comprise: if the weight of the transfusion bottle is smaller than the first preset weight, outputting a first alarming signal; if the weight of the transfusion bottle is smaller than the second preset weight, outputting a second alarming signal; so as to remind the patient of timely regulating the transfusion speed, call the medical staffs and the like, or to remind the medical staffs of timely conducting subsequent nursing works.

For example, as illustrated in FIG. 6a, in an example of the present embodiment, the operation method may comprise: installing a transfusion bottle; detecting a weight of the transfusion bottle and outputting the weight, for example, detecting the weight of the transfusion bottle in real time by a detector. The controller may determine whether the weight is greater than a first preset weight or not. If the weight is greater than the first preset weight, then proceeding with detecting the weight of the transfusion bottle; if the weight is smaller than the first preset weight, then determining whether the weight is greater than a second preset weight; if the weight is greater than the second preset weight, then controlling the transfusion speed regulator to lower the transfusion speed by the controller or outputting a first alarming signal through the first alarm device to remind the patient of calling the medical staffs for nursing works; if the weight is smaller than the second preset weight, then controlling the transfusion speed regulator to stop the transfusion by the controller, and also outputting a second alarming signal through the first alarm device to remind the patient of calling the medical staffs for nursing works. It is noted that, when the medical staffs are in the ward (round of ward), the first alarming signal and the second alarming signal may further remind the medical staffs of nursing the patient.

For example, as illustrated in FIG. 6b, in another example of the present embodiment, the operation method may comprise: installing a transfusion bottle; detecting a weight of the transfusion bottle and outputting the weight, e.g., detecting the weight of the transfusion bottle in real time and outputting the weight through a detector. It may transmit the weight to a monitoring platform through a controller, the monitoring platform may be disposed in, for example, a nursing station, and the controller may transmit the weight in wired or wireless manner. The monitoring platform determines whether the weight is greater than a first preset weight or not, if the weight is greater than the first preset weight, then proceeding with detecting the weight of the transfusion bottle; if the weight is smaller than the first preset weight, then determining whether the weight is greater than a second preset weight, if the weight is greater than the second preset weight, then sending a first control signal to the controller, controlling the transfusion speed regulator to lower the transfusion speed by the controller according to the first control signal, and also outputting a first alarming signal through a second alarm device to remind the medical staffs of conducting nursing works; if the weight is smaller than the second preset weight, then sending a second control signal to the controller, controlling the transfusion speed regulator to stop the transfusion by the controller according to the second control signal, and also outputting a second alarming signal through the second alarm device to remind the medical staffs of conducting nursing works. The nursing works may comprise, for example, regulating the transfusion speed, replacing the medical liquids, pulling out the needle or detecting the patient's body conditions and the like. It is noted that, when the weight is smaller than the first preset weight and greater than the second preset weight, the first alarm device may also output a first alarming signal; and when the weight is smaller than the second preset weight, the first alarm device may also output a second alarming signal; so as to remind the patient or the relatives of the patient of monitoring the transfusion conditions or call the medical staffs for nursing works and the like.

Of course, the foregoing specific implementations are merely to describe the transfusion monitoring system provided by the present embodiment. The embodiments of the present disclosure comprise but not limited thereto.

For the present disclosure, additional remarks as below may be noted:

I. The drawings of the embodiments of the present disclosure merely involve structures related to the embodiments of the present disclosure, and other structures may refer to common designs.

II. Thicknesses of layers or regions in the drawings describing the embodiments of the present disclosure may be magnified or reduced for purpose of clearness; that is, these figures are not drafted according to actual scales.

III. Without confliction, the embodiments of the present disclosure and the features in the embodiments can be combined with each other to attain new embodiments.

What is described above is related to the illustrative embodiments of the disclosure only and not limitative to the scope of the disclosure; the scopes of the disclosure are defined by the accompanying claims.

What is claimed is:
1. A transfusion speed regulator, comprising:
a housing, the housing comprising a bottom plate;
a lead rail on the housing, being unparallel to the bottom plate, the lead rail comprising a first lead rail and a second lead rail which are in parallel to each other;

a regulating roller configured to be moved along the lead rail to regulate a transfusion speed, the regulating roller comprising a shaft and a roller body, wherein both ends of the shaft are contacted with the first lead rail and the second lead rail respectively, and the roller body is sleeved onto the shaft and is between the first lead rail and the second lead rail; and an actuator configured to drive the regulating roller to move, the actuator comprising a stator and a rotator, wherein both of the stator and the rotator are between the shaft and the roller body, the shaft is coupled to the rotator, and the roller body is sleeved onto the stator.

2. The transfusion speed regulator according to claim 1, wherein the transfusion speed regulator is configured such that during the regulating roller moving along the lead rail, a distance between the regulating roller and the bottom plate is gradually varied in such a manner that a minimum distance between the regulating roller and the bottom plate is smaller than or equal to two times of a wall thickness of a transfusion tube, and a maximum distance between the regulating roller and the bottom plate is larger than or equal to an outer diameter of the transfusion tube in an uncompressed status.

3. The transfusion speed regulator according to claim 1, wherein an extending direction of the shaft is parallel to the bottom plate.

4. The transfusion speed regulator according to claim 1, further comprising a lead rod and a chute, wherein the chute extends along a direction parallel to the lead rail; and the lead rod is coupled to the stator and stretched into the chute.

5. A transfusion monitoring system, comprising a transfusion device, the transfusion device comprising:

a transfusion speed regulator, comprising:

a housing, the housing comprising a bottom plate;

a lead rail on the housing, being unparallel to the bottom plate and comprising a first lead rail and a second lead rail which are in parallel to each other;

a regulating roller configured to be moved along the lead rail to regulate a transfusion speed, the regulating roller comprising a shaft and a roller body, wherein both ends of the shaft are contacted with the first lead rail and the second lead rail respectively, and the roller body is sleeved onto the shaft and is between the first lead rail and the second lead rail; and an actuator configured to drive the regulating roller to move, the actuator comprising a stator and a rotator, wherein both of the stator and the rotator are between the shaft and the roller body, the shaft is coupled to the rotator, and the roller body is sleeved onto the stator;

a detector configured to detect a weight of a transfusion bottle and output the weight; and a controller configured to control the transfusion speed regulator to regulate the transfusion speed according to the weight.

6. The transfusion monitoring system according to claim 5, further comprising: a monitoring platform configured to receive the weight output from the detector and send a control signal for regulating the transfusion speed to the controller.

7. The transfusion monitoring system according to claim 6, wherein the controller is configured to control the transfusion speed regulator to lower the transfusion speed, if the weight is smaller than a first preset weight;

the controller is further configured to control the transfusion speed regulator to stop transfusing, if the weight is smaller than a second preset weight;

wherein the first preset weight is greater than the second preset weight.

8. The transfusion monitoring system according to claim 7, further comprising an alarm device configured to send an alarming signal, if the weight is smaller than at least one of the first preset weight and the second preset weight.

9. The transfusion monitoring system according to claim 8, wherein the alarm device is on at least one of the transfusion device and the monitoring platform.

10. The transfusion monitoring system according to claim 5, wherein the detector comprises an electronic weighing sensor.

* * * * *